United States Patent [19]

Lewtas et al.

[11] Patent Number: 5,117,679
[45] Date of Patent: Jun. 2, 1992

[54] TESTING APPARATUS AND METHOD

[75] Inventors: Kenneth Lewtas, Oxfordshire; Edwin W. Lehmann, Faringdon; John N. Mears, Oxfordshire; Brian H. Wiggins; Leslie G. Jones, both of Abingdon, all of England

[73] Assignee: Exxon Chemical Patents Inc., Linden, N.J.

[21] Appl. No.: 530,646

[22] Filed: May 30, 1990

[30] Foreign Application Priority Data

May 31, 1989 [GB] United Kingdom ............... 8912428

[51] Int. Cl.$^5$ .......................................... G01N 25/04
[52] U.S. Cl. ........................ 73/61.41 R; 374/17.0
[58] Field of Search .............. 73/61 R, 53, 64.1; 374/16, 17

[56] References Cited

U.S. PATENT DOCUMENTS

| | | |
|---|---|---|
| 3,008,324 | 11/1961 | Rayford et al. ............... 374/17 |
| 3,031,880 | 5/1962 | Findlay ........................ 374/17 |
| 3,447,358 | 6/1969 | Crespin et al. ................ 374/16 |
| 3,457,772 | 7/1969 | Chassagne et al. ............ 374/17 |
| 3,545,254 | 12/1970 | Chassagne et al. ............ 374/17 |
| 4,023,397 | 5/1977 | Ouvrard . | |

FOREIGN PATENT DOCUMENTS

| | | |
|---|---|---|
| 0030099 | 11/1980 | European Pat. Off. . |
| 0358403 | 3/1990 | European Pat. Off. . |
| 73659 | 5/1982 | Japan .................. 374/17 |
| 7550 | 1/1983 | Japan .................. 374/17 |
| 1418431 | 12/1975 | United Kingdom . |

OTHER PUBLICATIONS

Journal of The Institute of Petroleum, vol. 52, No. 510, Jun. 1966, pp. 173-185.
British Standard 2869, Fuel oils for non-marine use, Parts 1 & 2.

Primary Examiner—Hezron E. Williams
Assistant Examiner—Joseph W. Roskos
Attorney, Agent, or Firm—V. T. White

[57] ABSTRACT

A test device for assessing low temperature performance of a wax-containing fuel which compriss: a vessel for containing a fuel to be assessed, having cooling and heating elements, for cooling and heating the fuel in the vessel and a filter element wherein the fuel is caused to pass through the filter of the filter element and the cooling and heating elements are so arranged that a stable convection current is set up in the fuel and the filter is so positioned that it receives wax settling from the fuel.

9 Claims, 5 Drawing Sheets

TESTING APPARATUS AND METHOD

This invention relates to a device and method for assessing how well a diesel vehicle will operate at low temperature when using a fuel, taking into account the effect of formation of wax in the fuel, particularly a distillate petroleum fuel, at low temperature.

Crude and refined petroleum fuels, e.g., diesel fuel and heating oil, contain ranges of n-alkanes that separate out in the form of solid wax below the fuel cloud point (the temperature at which wax appears). For example, when a 0° C. cloud point diesel fuel is kept at below 0° C. for an extended period of time e.g., during a cold spell in winter, the wax crystallizes out into plate-like crystals that gel the fuel and prevent its passage through narrow pipes and filters. To lower the temperature at which wax crystallization limits the use and distribution of such fuels, certain wax crystal modifying additives are added to reduce the size and alter the shapes of wax crystals formed. For example, it is common practice to add low molecular weight copolymers of ethylene and unsaturated esters, in particular ethylene vinyl acetate copolymers (EVAC), to diesel fuels and heating oils. Using such additives formation of plate-like crystals of about 0.5 to 5 mm in size may be replaced by formation of needle-like crystals of about 20 to 25 $\mu$m in length. As a result of using such EVAC additives, the gel no longer forms and the fuel with wax may still be used several degrees below its cloud point. The fuel will still flow and most diesel vehicles will continue to operate down to a lower temperature than would be possible without the additives.

To assess the quality of a fuel, and in particular its performance at low temperature, a test is carried out to measure the temperature at which the crystallized wax blocks or plugs a filter. This temperature is known as the Cold Filter Plugging Point (CFPP). Many countries set standards for CFPP which must be met by oils and fuels. The test is described in BS 2869, and in "Journal of the Institute of Petroleum", 52 (1966) 173 to 185, the disclosure of both of which is incorporated by reference herein, and is carried out by sucking the oil or fuel through a filter and observing the temperature at which the filter becomes blocked by wax.

Whilst this test assesses the continuous flow properties of the fuel, there are discrepancies between the performance temperature indicated by the CFPP tests and the operability of diesel fuelled vehicles at low temperatures.

Prolonged storage at sub-cloud temperature, e.g., 10° C. below the cloud point, will result not only in wax crystallization but, if the fuel remains static for e.g., several days at this temperature, then the wax crystals will settle and agglomerate at the base of the fuel storage tank. This effect also occurs overnight in a diesel vehicle fuel tank. A practical result of this phenomenon is that some diesel vehicles will show premature failures at temperatures above the fail temperature in the absence of wax settling. Also, fuel in exposed storage tanks will become inhomogeneous, delivering wax enriched fuel at times (with related cold flow problems) and wax depleted fuel at other times. To alleviate this problem a wax anti-settling agent (WASA) such as is described in EP-A-0030099, may be added to the fuel.

Additionally, modern additives in some cases do not behave in the same way as older additives and old CFPP correlations may no longer be appropriate Accordingly it is necessary to model more closely practical cooling rates, filter surfaces and fuel behaviour As indicated above, the CFPP test does not take into account wax settling and departs from realistic cooling conditions. Above the CFPP fail temperature most diesel vehicles will have no operability problems if there is no wax settling. However, if wax settling occurs, this may cause engine failure at temperatures above the CFPP. The CFPP test thus can suffer from the disadvantage that two fuels which have the same cold filter plugging point will not necessarily show the same tendency for the wax crystals to settle. Additionally, if the CFPP test is used outside inconveniently tight limits, then as a result of the way it departs from real world conditions it can overestimate fuel and vehicle resistance to wax induced failure.

A test as described in EP-A-0030099 was therefore devised to assess the amount of settling of wax in a fuel; this assessment method simulated the conditions in a fuel tank. A sample of the fuel in a graduated flask was gradually cooled, e.g., at the rate of 1° C./hour, to the test temperature to ensure that the size and shape of crystals formed corresponded with the size and shape of crystals formed in practice. Once the test temperature, generally 5 to 15° C. below the cloud point of fuel, was reached, the fuel was held at the temperature for three to five days allowing the crystals to settle under gravity in the same way they would in a fuel tank.

However, this test is time consuming and does not allow rapid assessment of the wax settling properties of a fuel. As such, it cannot be used at a refinery, where an assessment would be required fairly rapidly.

There is now a very great need to speed up the test. Unfortunately no reasonably accurate waxing test can now be proposed that involves CFPP-type cooling rates, which at around 40° C./hour are very much faster than those seen in the field. This is because different additive types ( are influenced by cooling rate to different extents—but the effect is not at all consistent. In fact, even at 8-10° C./hour—the top end of field cooling rates—loss of additive discrimination has been seen.

The present invention provides a modification of the CFPP test which better correlates with vehicle operating conditions and makes allowances for wax settling.

The present invention provides a device for assessing the low temperature performance of a wax-containing fuel, the device comprising a vessel for containing fuel to be assessed, cooling means for cooling fuel in the vessel, a filter element, fuel transfer means for causing fuel in the vessel to pass through the filter element, and means for generating a predetermined convection current in the fuel when it is contained in the vessel, the filter element being so positioned that in use, at least when the fuel transfer means is in operation, and preferably always, the element preferentially receives wax settled or settling from the fuel.

The present invention further provides a method of measuring the low temperature performance of a wax-containing fuel comprising generating a consistent or stable convection current in the fuel while cooling it and when a predetermined temperature has been reached causing the fuel to pass through a filter located in relation to the convection current preferentially to receive any wax settled or settling from the fuel.

The present invention accordingly makes it possible to assess the low temperature performance of wax-containing fuels using a cooling cell in which is placed a test vessel for the fuel sample, in which is submerged a filtration module through which fuel may be withdrawn downwards under vacuum, the test jar being provided, preferably externally, with a heating means and a cooling means to provide a controlled cooling rate, with a temperature differential within the fuel resulting in convection currents within the fuel sample.

The invention further provides a filter module for the use in the device of the invention, which comprises a circular cylindrical block having a tubular member mounted with its axis parallel to but spaced from that of the cylinder on one end face of the block, and on the opposite, or preferably the same, end face is formed a threaded socket suitable for receiving a filter element, the axis of the socket being parallel to and spaced from the axes of the tube and the block, and a passageway between the tube and the bottom of the socket.

Advantageously, the fuel is cooled at a predetermined rate, preferably from a predetermined temperature, to the predetermined test temperature. If desired, the fuel may be maintained at the test temperature for a predetermined time before carrying out the test by causing the fuel to pass (or attempt to pass) through the filter.

The filtration module conveniently consists of a cylindrical block slightly smaller in diameter than a standard CFPP test jar. On one side of the block is located the filter, and on the other a vertical stalk-like tube which in use is topped with a standard CFPP pipette, through which vacuum may be applied. Typically vacuums ranging from 10 to 70 kPa but preferably from 13 to 18 kPa are applied in a controlled way, e.g., 9 kPa at 10 to 11 seconds after the start of the test and 13 to 18 kPa at 24 to 28 seconds. Application of the vacuum may be varied from "instant" to "very gradual", e.g., over 60 seconds, to vary the severity of the test.

This preferred configuration enables the filtration module to be interchanged with CFPP test heads, enabling standard CFPP pipettes and testing equipment to be used with the head according to the invention The cell is preferably a standard unit of the type traditionally used in the CFPP test (with auxiliary modifications—extra vacuum line, nitrogen purge, changeover valves) into which a sleeve is fitted in place of the normal test jar carrier. The sleeve incorporates a controlled electric heater, mounted opposite a copper block, which enables the cell cooling rate to be accurately controlled while maintaining a temperature difference, which may be varied, across the cell forcing the contents to circulate by controlled, natural convection —so tending to promote wax settlement on or near the filter.

The means for generating a convection current advantageously comprises the cooling means and a heater positioned to heat part only of the vessel, the heating means preferably being positioned to heat one side only of the vessel while the cooling means is positioned to cool an opposite side.

The vessel is advantageously a circular cylinder that in use is upright, the heating means being located to heat a part of the circumference forming a first arc of the circle, the cooling means being located to cool a second arc of the circle, and the filter element being positioned within the sector subtended by the second arc. The filter element is preferably positioned at the bottom of or below the bottom of the downward part of the predetermined convection current path.

The cell conveniently comprises a traditional CFPP type cooling cell, and the temperature controlled sleeve provided by the invention is made to be a snug fit. This ensures consistent cooling conditions for all samples. (It may be necessary to specially select test jars to fit inside the sleeve.)

The filter head is advantageously set facing upwards, preferably on the cold side of the test jar, preferably positioned immediately below the downward part of the convection current path that is set up while the device is being cooled, with the heater on, before application of the vacuum, which constitutes the preferred fuel transfer means, so as to capture the maximum amount of settled wax on the filter surface so that the fuel withdrawn by the vacuum through the filter needs to pass through any settled wax there may already be on the filter head. In addition, the wax that is present in the withdrawn sample will also settle on the head. It will be appreciated that operation of the fuel transfer means interferes with convection currents set up.

One form of device and module constructed in accordance with the invention will now be described in greater detail, by way of example only, with reference to the accompanying drawings, in which.

Figure 1:
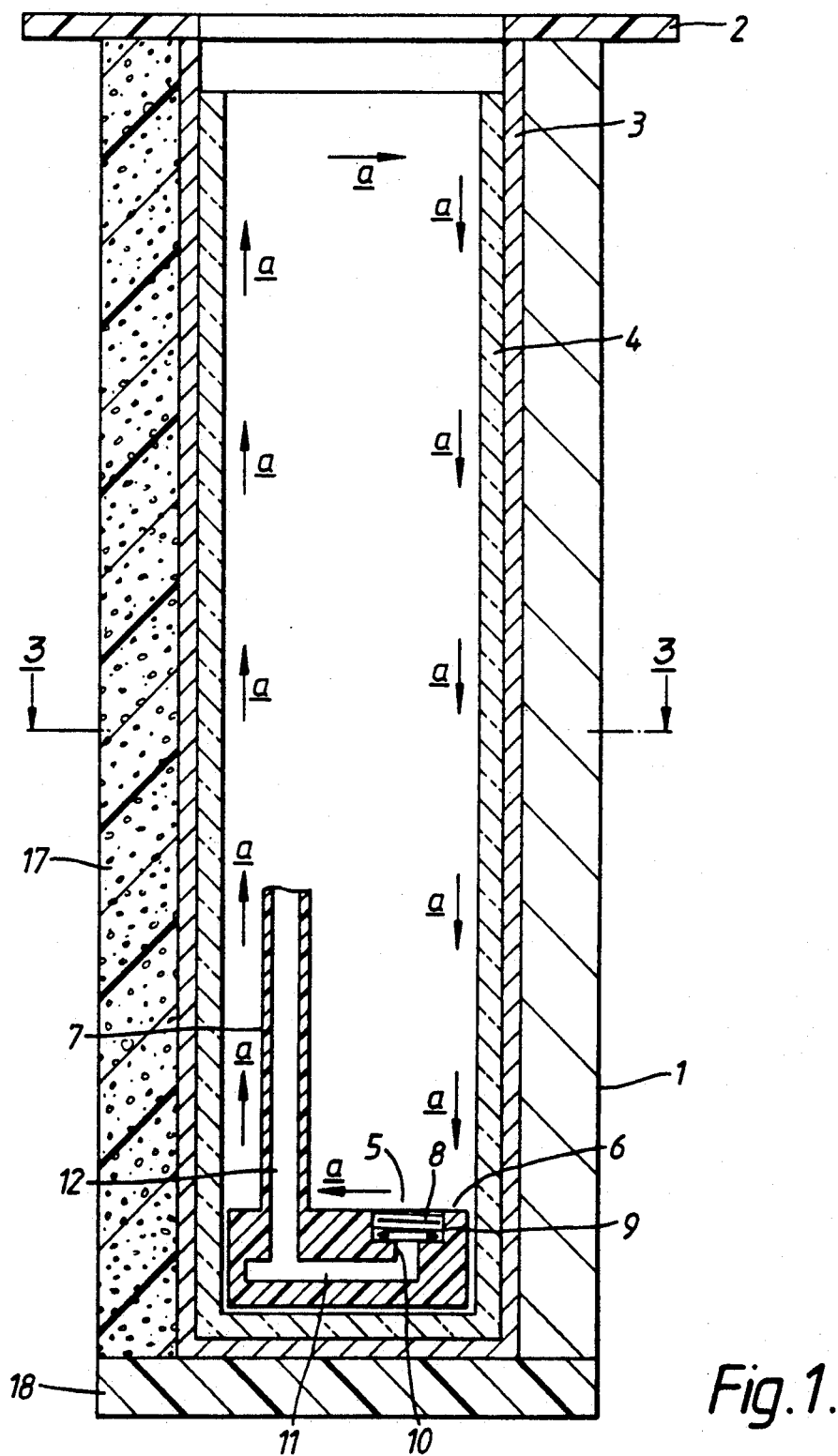
FIG. 1 is a vertical section of a device constructed according to the invention.
Figure 2:
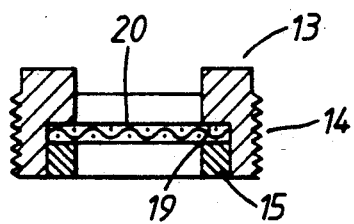
FIG. 2 is an enlarged section of a filter element for use in the device.

Referring to FIGS. 1 and 2, a semi-cylindrical metal block 1 is provided with a plastics flange 2 and a plastics base 18, both conveniently of nylon. The block 1 carries an inner metal cylinder 3 secured thereto, together with insulation 17, by the flange and the base 18. Surrounding the block 1 and insulation 17 is an outer brass cylinder (not shown) to provide containment. Snugly fitting within cylinder 3 is a glass test jar 4. Within the jar 4 is mounted a filter module 5 which comprises a cylindrical block part 6 and a tube part 7 integrally connected to one another. The block part 6 has a cavity 8 with an internal thread 9 and an 0-ring seal 10 mounted therein. The cavity 8 communicates with an internal bore 11 which in turn communicates with a bore 12 of tube part 7 of filter module 5. The tube part 7 is connectable to a vacuum line (not shown).

Referring to FIG. 2, a filter element 13 has an external thread 14 corresponding to the internal thread 9 of the cavity 8. The element 13 has an internal flange 19 and a force fitted sleeve 15 between which a filter 20 is retained. The filter 20 is conveniently a mesh with nominal openings of 45 or 25 $\mu$m. The element 13 is screwed into block part 6 of filter module 5 (see FIG. 1) by means of corresponding threads 9 and 14. (The element 13 is shown separately in FIG. 2 rather than in FIG. 1 for reasons of clarity.)

Figure 3:
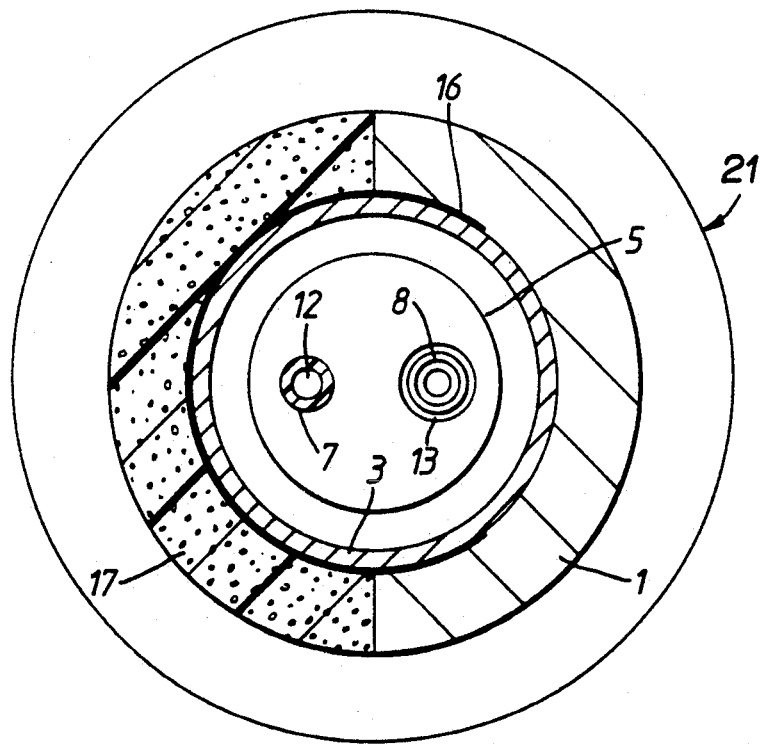
FIG. 3 is a section on the line A—A of FIG. 1.

Referring to FIG. 3, heating and cooling means not shown in FIG. 1 and 2 are depicted. The jar 4 is not shown. Positioned between the metal block 1 and the inner metal cylinder 3, and on the cylinder 3, is a heating element 16 in the form of a plastics sheet having heater foils and a temperature sensor embedded therein. The element 16 extends only part of the way round the inner cylinder 3 and is connectable to a controlled source of electrical power (not shown). Also shown in FIG. 3 is the insulation material 17 advantageously of foam which is provided adjacent to part of the heating element 16, and as a result the block 1 does not totally embrace the metal cylinder 3. Where it does embrace the cylinder 3, it transfers heat from it to a surrounding cooling tank (21).

In operation of the device shown in FIGS. 1, 2 and 3, fuel to be tested is placed in jar 4, and the device cooled at a desired rate by means of heat transfer to the surrounding tank cooled by a refrigeration device (not shown). The heating element 16 is energized: since it extends only part way about the test jar 4, part of the fuel therein is heated and part is cooled so that convection currents are set up within the fuel as illustrated by the arrows a in FIG. 1. The filter element 13 is positioned asymmetrically, adjacent to the cooled side of jar 4, and hence preferentially receives any wax in the fuel on its filter 20. When the fuel in the jar 4 has cooled to a predetermined temperature, measured by a thermometer (not shown) positioned above the surface, e.g., some 45 mm above the surface, of the filter 20, and a stable convection current has been set up as a result of the heating at one side of the cylinder and cooling on the opposite side, a vacuum is applied via the pipe part 7 to draw fuel into the cavity 8 through the filter 20, along the bore 11, through the bore 12 of the pipe part 7, and into a standard CFPP pipette (not shown) attached to the top of the pipe part 7.

The ability of the fuel to pass through the filter 20 and into the pipette in 60 seconds is taken as a measure of performance of the fuel at the test temperature: if 20 ml passes into the pipette within 60 seconds the fuel passes the test and if less than 20 ml pass within that time it fails. The test is a "one off" test as indicated herein.

During the run, strong "double convection" patterns are set up—that is convection patterns reinforced by the greater density of the wax with respect to the fuel. As a result, wax is deposited preferentially over the filter, rather than evenly over the base as the test jar.

The strength of the convection current may be controlled by the temperature difference across the test jar. Preferably differences of between 2° C. and 6° C. are maintained. Not only does the test predict vehicle operability better than the CFPP by virtue of using more accurate cooling rates, but also accentuates wax settlement over the filter and, by convection, causes temperature cycles within the fuel.

Temperature differences may be varied by changing areas of heating and cooling surface in the sheath, and varying the thickness and materials of construction used in the metal block 1 and the inner metal cylinder 3. The efficiency of the heater insulation, and power output of the heater, may also be varied.

In operation the temperature probe is located above the filter surface, the sheath assembly is inserted and the vacuum set to be, for example, a nominal 15 kPa after 30 seconds of test. The test head is then inserted and the temperature set to be that at which fuel operability is to be evaluated. The heater on the hot side combined with the design of the insulation and the metal conducting parts ensure a temperature differential across the fuel as it cools of, for example, between 2 and 6° C. The system is then set to cool steadily and continuously to the overall test temperature at the desired cooling rate and the measurement made of the ability of the fuel to pass through the filter at the desired temperature.

The use of the test device is illustrated in the following examples which compare the results obtained at a cooling rate of 2° C. per hour, using a 45 μm filter, with those obtained by cold chassis dynamometer testing.

Figure 4:
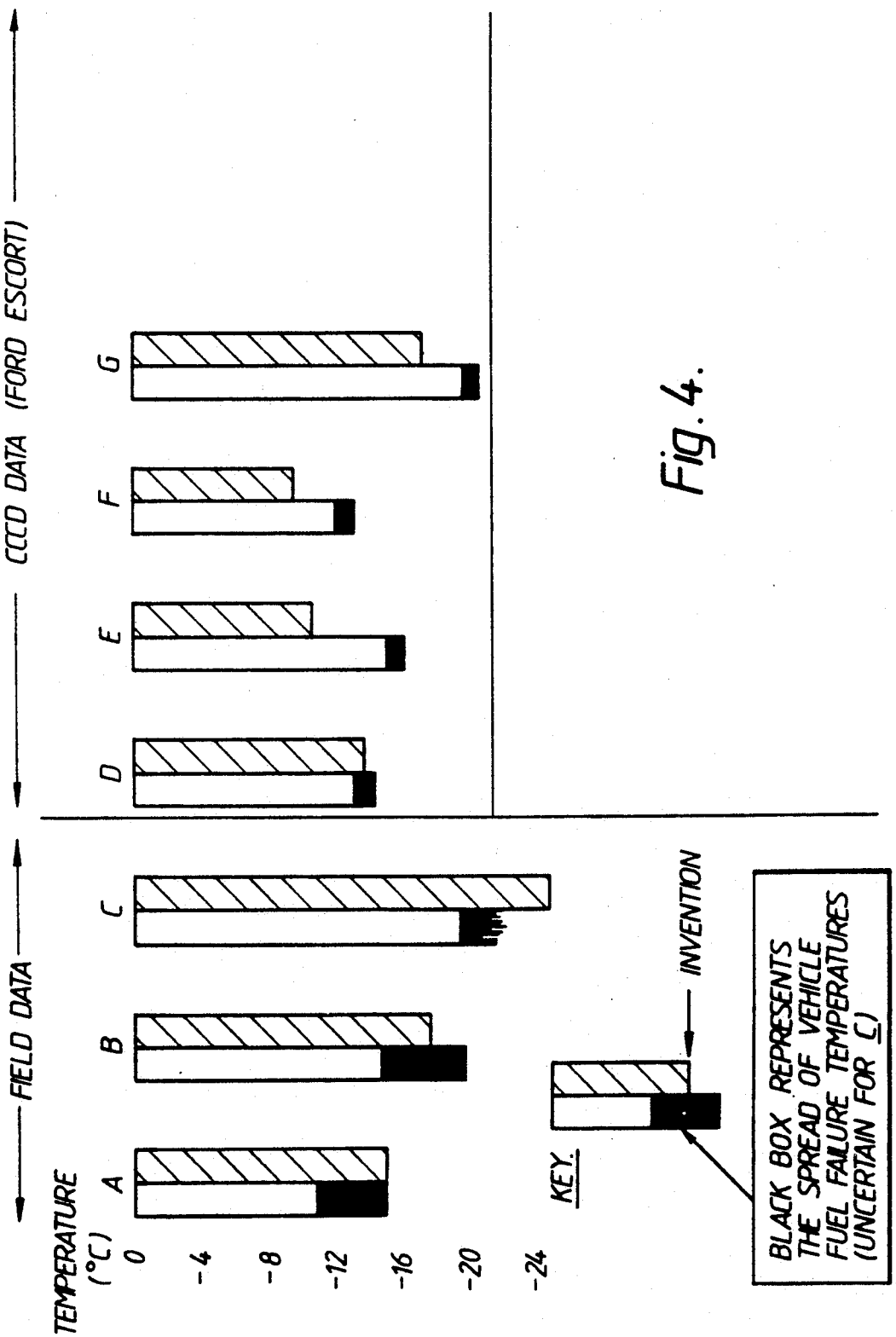
FIG. 4 shows a comparison of results obtained by the method of the invention and field trials.

FIG. 4 shows the results comparing field trials and CCCD (cold climate chassis dynamometer) data using various fuels. The field operability data set A, B and C represents 6 vehicle types, A using a conventional ethylene vinyl acetate copolymer flow improver, B using a wax antisettling additive package and C the additive combination as described in EP-A-30099. The CCCD data sets D to G using four different fuels use the most critical vehicle—the same as the most critical field trial type, the 1987 model Ford Escort.

The field data show that, in the three fuels treated with different additive types, the values obtained using the test methods of the invention correspond to general performance levels.

In contrast, in the CCCD test program, the test of the present invention was generally slightly more severe than the dynamometer results—averaging 1.9° C. more severe, with a standard deviation of 2.2° C. This means that, on this set of results, there is a 5% chance of the most severe vehicle's CCCD result for a given fuel being 2.5° C. or more above the operability temperature indicated using the techniques of the present invention. This difference coincides with the margin by which field air temperatures are generally below fuel temperature—and the data all involve fuel temperature to ensure consistent results. Accordingly, the value recorded by the test according to the invention may be regarded as a limiting air temperature for satisfactory operation, instead of the actual fuel temperature.

Figure 5:
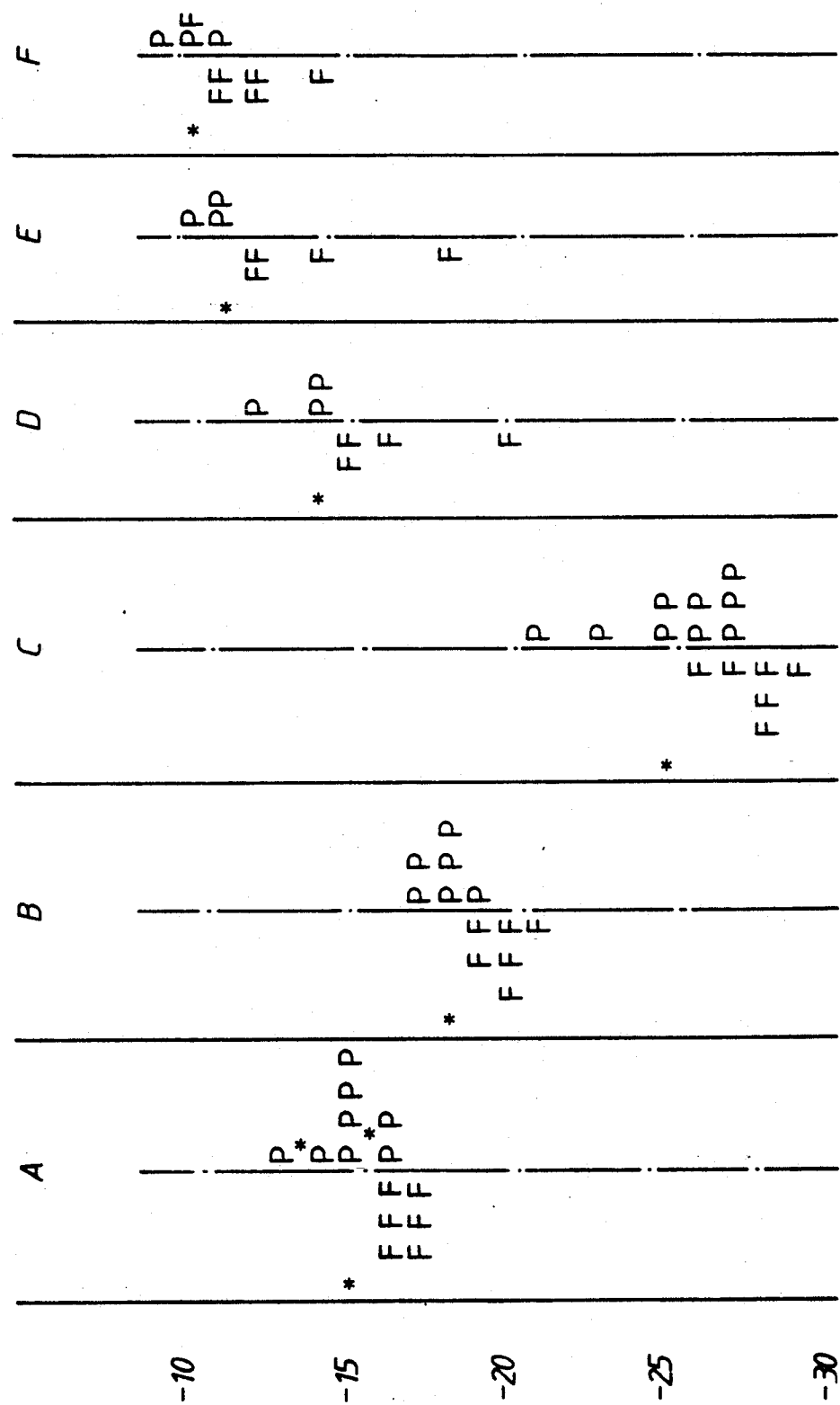
FIG. 5 shows the individual results obtained in the method of the invention.

Individual results are shown in FIG. 5, the fuels and additives used in A, B and C of FIG. 5 being the same as those in FIG. 4. "P" represents a PASS result, and "F" a fail, in the test of the invention, there generally being a number of tests at each of the important temperatures. An asterisk indicates the "plugging point" temperature recorded for the test. The results show that test consistency is good.

Figure 6:
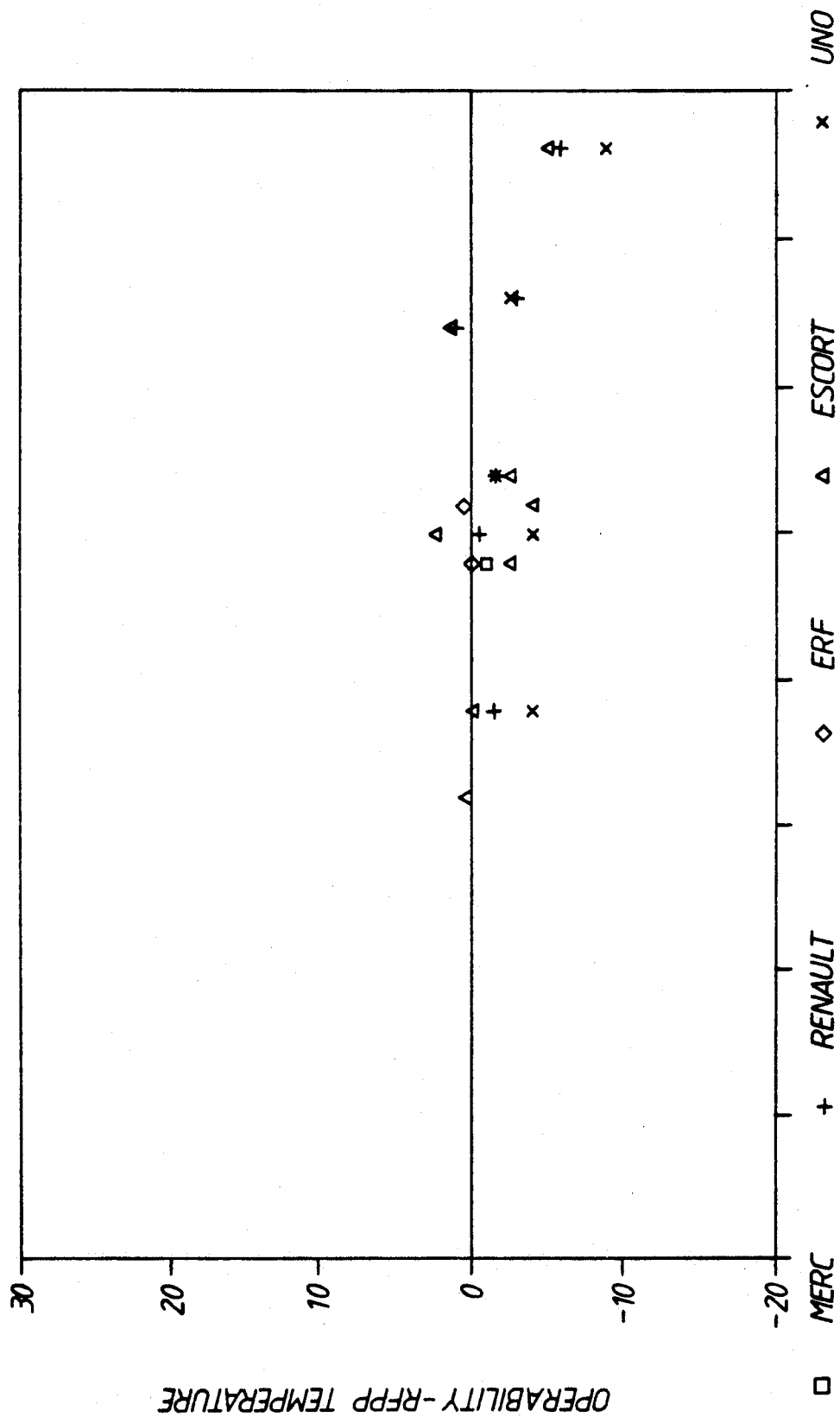
FIG. 6 shows a comparison between results obtained by the method of the invention and field trials using different vehicles.

FIG. 6 shows a comparison between the operability temperature as measured by a field test and the results achieved using the test of the invention for various vehicles, again showing good correlation.

What is claimed is:

1. A device for assessing the low temperature performance of a wax-containing fuel, the device comprising a vessel for containing fuel to be assessed, cooling means for cooling fuel in the vessel, a filter element, fuel transfer means for causing fuel in the vessel to pass through the filter element, and means for generating a predetermined convection current in the fuel when it is contained in the vessel, the filter element being so positioned that in use, at least when the fuel transfer means is in operation, the element preferentially receives wax settled or settling from the fuel.

2. A device as claimed in claim 1, wherein the element comprises a horizontal filter and the fuel transfer means causes fuel to pass downwardly through it.

3. A device as claimed in claim 1 wherein the element is positioned in or below the downward part of the convection current path.

4. A device as claimed in claim 1, wherein the means for generating a convection current comprises the cooling means and a heater positioned to heat part only of the vessel.

5. A device as claimed in claim 4, wherein the heating means is positioned to heat one side only of the vessel and the cooling means is positioned to cool an opposite side.

6. A device as claimed in claim 4, wherein the vessel is a circular cylinder that in use is upright, the heating means is located to heat a part of the circumference forming a first arc of the circle, the cooling means is located to cool a second arc of the circle, and the filter element is positioned within the sector subtended by the second arc.

7. A device as claimed in claim 6, wherein the filter element is positioned at the bottom of or below the bottom of the downward part of the predetermined convection current path.

8. A filter module for the use in the device of claim 1, which comprises a circular cylindrical block having a tubular member mounted with its axis parallel to but spaced from that of the cylinder on one end face of the block, on the same end face there being formed a threaded socket suitable for receiving a filter element, the axis of the socket being parallel to and spaced from the axes of the tube and the block, and there being a passageway between the tube and the bottom of the socket.

9. A method of measuring the low temperature performance of a wax-containing fuel comprising generating a stable convection current in the fuel while cooling it and when a predetermined temperature has been reached causing the fuel to pass through a filter located in relation to the convection current preferentially to receive any wax settled or settling from the fuel.

* * * * *